(12) United States Patent
Christenhusz et al.

(10) Patent No.: US 8,118,764 B2
(45) Date of Patent: Feb. 21, 2012

(54) HIP ABDUCTION ORTHOSIS

(75) Inventors: Harry Plechelmus Christenhusz, Bad Bentheim (DE); Lambertus Joseph Martinus Kruijsen, Uden (NL)

(73) Assignee: Ossur Europe B.V., Son (NL)

( * ) Notice: Subject to any disclaimer, the term of this patent is extended or adjusted under 35 U.S.C. 154(b) by 739 days.

(21) Appl. No.: 11/989,358

(22) PCT Filed: May 12, 2006

(86) PCT No.: PCT/NL2006/000247
§ 371 (c)(1),
(2), (4) Date: Dec. 12, 2008

(87) PCT Pub. No.: WO2007/008058
PCT Pub. Date: Jan. 18, 2007

(65) Prior Publication Data
US 2009/0216165 A1    Aug. 27, 2009

(30) Foreign Application Priority Data

Jul. 12, 2005  (NL) .................................... 1029502
Mar. 10, 2006  (NL) .................................... 1031342

(51) Int. Cl.
*A61F 5/00*  (2006.01)
*A61F 5/37*  (2006.01)

(52) U.S. Cl. .............................. 602/24; 602/19; 128/870

(58) Field of Classification Search .................. 128/882, 128/883, 869, 845, 847, 870, DIG. 15; 602/19, 602/16, 20, 23, 26, 4, 24
See application file for complete search history.

(56) References Cited

U.S. PATENT DOCUMENTS 3,260,259 A * 7/1966 Connelly ........................ 602/24
4,574,790 A * 3/1986 Wellershaus .................... 602/24
4,901,710 A * 2/1990 Meyer ............................ 602/24

FOREIGN PATENT DOCUMENTS

EP    0237242    9/1987
EP    1159940    12/2001

* cited by examiner

*Primary Examiner* — Patricia Bianco
*Assistant Examiner* — Ophelia Hawthorne
(74) *Attorney, Agent, or Firm* — Bacon & Thomas, PLLC

(57) ABSTRACT

A hip abduction orthosis for stabilizing the hip joints of a user, provided with a trunk engaging part, first and second thigh engaging parts and first and second coupling parts, wherein the first coupling part connects the first thigh engaging part with the trunk engaging part and the second coupling part connects the second thigh engaging part with the trunk engaging part. A distance between the first and/or the second thigh engaging part and the trunk engaging part is settable. An abduction angle of that thigh engaging part is settable. The distance and the abduction angle are coupled such that a first set distance between that thigh engaging part and the trunk engaging part is coupled with a first set abduction angle and a second set distance different from the first set distance is coupled with a second set abduction angle different from the first set abduction angle.

55 Claims, 5 Drawing Sheets

HIP ABDUCTION ORTHOSIS

This application is the U.S. National Phase of, and Applicants claim priority from, International Application Number PCT/NL2006/000247 filed 12 May 2006 and Netherlands Applications bearing Serial No. 1029502 filed 12 Jul. 2005 and Serial No. 1031342 filed 10 March 2006, which are incorporated herein by reference.

BACKGROUND OF THE INVENTION

The invention relates to a hip abduction orthosis for stabilizing the hip joints of a user, provided with a trunk engaging part, a first and second thigh engaging part and a first and second coupling part, wherein the trunk engaging part is arranged to be connected with a trunk of the user, wherein the first and second thigh engaging part are arranged for engaging a first and second thigh of the user, respectively, wherein the first coupling part connects the first thigh engaging part with the trunk engaging part and the second coupling part connects the second thigh engaging part with the trunk engaging part, and wherein a distance between the first and/or second thigh engaging part and the trunk engaging part is settable, wherein an abduction angle of that thigh engaging part is included between a line which operatively extends in the longitudinal direction of that thigh and through a plane of that thigh engaging part which operatively abuts that thigh and the sagittal plane, and wherein the abduction angle of that thigh engaging part is settable.

Such hip abduction orthoses are known per se and are, for instance, used for treating hip dysplasia or stabilizing the hips after (sub)luxation. Here, in general, both legs of the user are brought into a straddle, which means that the knees of the legs are placed at a distance from each other. The hip abduction orthoses are, for instance, used with small children.

The known hip abduction orthoses have the drawback that setting a correct position, for correctly stabilizing the hip joints, of the thigh engaging parts with respect to the trunk engaging part is complicated and requires a thorough knowledge of the orthosis and/or the disorder. For a user, or if the hip abduction orthosis is used with a small child, for a caretaker (like a parent) of the user, it is therefore difficult to set the orthosis. If therefore, for instance by accident, the orthosis becomes unset or if the orthosis is to be set otherwise, for instance because the child has grown, it is necessary to enlist the aid of specialized staff to set the orthosis. This entails extra costs and possibly a time delay between the orthosis becoming unset and the orthosis being again set correctly.

It is an object of the invention to obviate above problem.

SUMMARY OF THE INVENTION

To this end, according to the invention, a hip abduction orthosis is provided where the distance and the abduction angle are coupled such that a first set distance between that thigh engaging part and the trunk engaging part is coupled with a first set abduction angle and a second set distance different from the first set distance is coupled with a second set abduction angle different from the first set abduction angle.

Here, the term "distance" is used to refer to the variable distance between a thigh engaging part and the trunk part. Here, the term "set distance" is used to refer to a specific, set value of the distance between that thigh engaging part and the trunk part. Likewise, here, the term "abduction angle" is used to refer to the variable abduction angle of a thigh engaging part, and, here, the term "set abduction angle" is used to refer to a specific, set value of the abduction angle of that thigh engaging part.

Thus if, with the orthosis, the distance between the thigh engaging part and the trunk engaging part is adjusted to a dimension of the user, i.e. is set at the first set distance, the orthosis automatically sets the first abduction angle at the first set abduction angle coupled with the first set distance. Setting the distance at the first set distance therefore results in the abduction angle being set at the first set abduction angle. If, for instance, the orthosis accidentally becomes unset, by setting the distance at the first set distance, directly the right combination of the first set distance and the first set abduction angle coupled therewith is obtained. If, for instance, the user has grown, by setting the distance at the second set distance, directly the right combination of the second set distance and the second set abduction angle coupled therewith is obtained.

It is possible for the hip abduction orthosis for steplessly setting the distance between the first and/or second thigh engaging part and the trunk engaging part within a predetermined range of distances. Thus, it is possible to provide the set distance which corresponds well to a dimension of the user, for instance a length of the thigh of the user.

It is also possible for the hip abduction orthosis to be arranged for setting the distance between the first and/or second thigh engaging part and the trunk engaging part in a plurality of steps. Thus, it is possible to provide the set distance which corresponds well to a dimension of the user and can simply be set.

Preferably, the distance and the abduction angle are coupled such that each set distance is coupled with an abduction angle coupled therewith. Thus, by setting the distance, for each set distance, directly the right combination of the set distance and the set abduction angle coupled therewith is obtained. Thus, the hip abduction orthosis can be set in a simple manner.

Preferably, a change of the distance within a predetermined distance range results in a predetermined change of the abduction angle. Thus, by changing the distance, the abduction angle is changed as well and thus, by setting a changed set distance, a changed set abduction angle is also obtained.

Preferably, each change of the distance within the predetermined distance range results in a predetermined change of the abduction angle. Thus, with each change of the distance, a change of the abduction angle is obtained, so that, for each distance, a desired abduction angle can be prescribed by the hip abduction orthosis.

Preferably, each set distance is unambiguously coupled with the set abduction angle coupled therewith. Thus, it is not the case that one distance is coupled with multiple abduction angles, or one abduction angle is coupled with multiple distances. Thus, if a desired distance and/or abduction angle is known, the orthosis can be set in a simple manner.

Preferably, the distance and the abduction angle are coupled such that, if the set distance increases, the abduction angle coupled therewith decreases. It has been found that, for instance for treating hip dysplasia in children, it is, in practice, favorable to have an abduction angle imposed by the orthosis decrease gradually during the treatment. Since the child will grow during the treatment, therefore, because if the set distance increases the set abduction angle coupled therewith decreases, it is achieved that, during the treatment, the orthosis will automatically be set correctly when the distance is each time adjusted to the dimension of the child. Preferably, then the distance and the abduction angle are coupled such that, with respect to the trunk engaging part, that thigh engaging part is movable along a curved path, such as an arc.

Preferably, at least in top plan view, the first and the second thigh engaging part are movable along one and the same arc. Thus, a very favorable variation of the set abduction angle with increasing set distance is obtained.

For the treatment of hip dysplasia in children, the thigh engaging parts are preferably positioned with respect to the trunk engaging part such that, in use, the upper legs extend transversely to the trunk, more preferably such that the upper legs recede at a small angle of, for instance, about 12°, downwards (in the direction from the head to the hip of the user) going from the hip to the knee.

In a special variant, a height position of at least one thigh engaging part is settable in a height direction of the user. It is thus possible to have the upper leg extending transversely to the trunk recede slightly upwards (in the direction from the hip to the head of the user) going from the hip to the knee, or have it recede slightly downwards (in the direction from the head to the hip of the user) going from the hip to the knee. As a result, the hip abduction orthosis cannot only be used for normal hip dysplasia but also for more specific hip defects.

Preferably, the distance, the abduction angle and the height position are coupled such that the first set distance between that thigh engaging part and the trunk engaging part is coupled with the first set abduction angle and a first set height position and the second set distance different from the first set distance is coupled with the second set abduction angle different from the first set abduction angle and a second set height position optionally different from the first set height position.

Here, the term "height position" is used to refer to the variable height position of a thigh engaging part. Here, the term "set height position" is used to indicate a specific, set value of the height position of that thigh engaging part.

Thus if, with the orthosis, the distance between the thigh engaging part and the trunk engaging part is adjusted to a dimension of the user, i.e. is set at the first set distance, the orthosis automatically sets the abduction angle and the height position at the first set abduction angle and the first set height position coupled with the first set distance. If, for instance, the orthosis accidentally becomes unset, by setting the distance at the first set distance, directly the right combination of the first set distance and the first set abduction angle and first set height position coupled therewith is obtained. If, for instance, the user has grown, then by setting the distance at the second set distance, directly the right combination of the second set distance and the second set abduction angle and second set height position coupled therewith is obtained.

Preferably, the distance, the abduction angle and the height position are coupled such that the thigh engaging part is movable along a fixed predetermined path with respect to the trunk engaging part. Thus, by setting the distance, for each set distance, directly the right combination of the set distance and the set abduction angle and set height position coupled therewith is obtained. Thus, the hip abduction orthosis can be set in a simple manner.

Preferably, the fixed predetermined path recedes in lateral direction downwards away from a transversal plane through the hip balls of the user. Thus, in use, the upper leg associated with that thigh engaging part recedes in lateral direction downwards away from the transversal plane, so that that upper leg has a favorable orientation with respect to the hip.

Preferably, the first and/or second coupling part is provided with a guide for guiding the first and/or second thigh engaging part from the first set distance and the first set abduction angle coupled therewith to the second set distance and the second set abduction angle coupled therewith. Thus, a distance, abduction angle and optionally height position of the first and/or second thigh engaging part can be set in a simple manner.

Preferably, the hip abduction orthosis is provided with distance indicating means for showing the set distance between that thigh engaging part and the trunk engaging part. Thus, for the user, it is very simple to set the desired distance and it is not necessary to measure the set distance.

Preferably, the distance indicating means show a distance between the two backs of the knees of the user corresponding with the set distance. Thus, it is possible to measure the distance between the two backs of the knees of the users and to then correctly set the hip abduction orthosis in a simple manner, i.e. to correctly set the distance, the abduction angle and optionally the height position.

Preferably, at least one thigh engaging part has a conical shape when it has been applied to a thigh of the user. Thus, a comfortable thigh engaging part is provided which corresponds with the natural shape of the thigh and can keep that thigh engaging part positioned well.

Preferably, at least one thigh engaging part comprises a bistable element for keeping that thigh engaging part opened in a first stable condition for being able to place a thigh therein and keeping that thigh engaging part substantially closed in a second stable position for at least partly enclosing a thigh. This offers the advantage that the thigh engaging part can be applied to the thigh particularly simply. This is because it is possible to keep the thigh engaging part opened in the first stable condition and then place the thigh in the opened thigh engaging part. The thigh engaging part will not fall shut before the thigh has been placed in the thigh engaging part, so that placing the thigh is not hindered. Then, it is possible keep the thigh engaging part substantially closed in the second stable condition and to close the thigh engaging part around the thigh, for instance with the aid of a snap closure.

Preferably, a circumferential dimension of a thigh engaging part is settable. It is thus possible to adjust the thigh engaging part to a dimension of the user.

Preferably, the thigh engaging part is provided with circumference indicating means for showing the set circumferential dimension. Thus, for the user, it is very simple to set the desired circumferential dimension and it is not necessary to measure the set circumferential dimension.

Preferably, the at least one thigh engaging part and/or the trunk engaging part comprises a substantially rigid molded part, for instance manufactured from plastic. This has the advantage that a strong thigh engaging part and/or trunk engaging part is provided for being able to strongly attach the thigh engaging part and/or trunk engaging part to the user.

Preferably, at least one thigh engaging part and/or the trunk engaging part is provided with a cushion from a flexible and/or elastic material, such as plastic, which operatively faces the user. Thus, a resilient and/or soft contact surface is created against which the user lies, which increases the wearing comfort.

Preferably, the thigh engaging part and/or the trunk engaging part is manufactured by means of multi-component injection molding for simultaneously molding the cushion and the molded part. This is because it is thus possible to simultaneously injection-mold a molded part from solid plastic and a cushion from resilient plastic, which allows an inexpensive manufacture of the thigh engaging part and/or trunk engaging part.

Preferably, the orthosis is substantially completely manufactured from plastic. Thus, an orthosis is provided which can be manufactured simply and inexpensively. This orthosis can also be cleaned simply, for instance with water.

BRIEF DESCRIPTION OF THE DRAWINGS

In the following, the invention is, by way of example, explained in more detail with reference to the drawing, in which:

FIG. 1b shows a bottom view of the hip abduction orthosis shown in FIG. 1a;

In the drawing, corresponding parts are designated by corresponding reference numerals.

DETAILED DESCRIPTION OF THE INVENTION

Figure 1A:
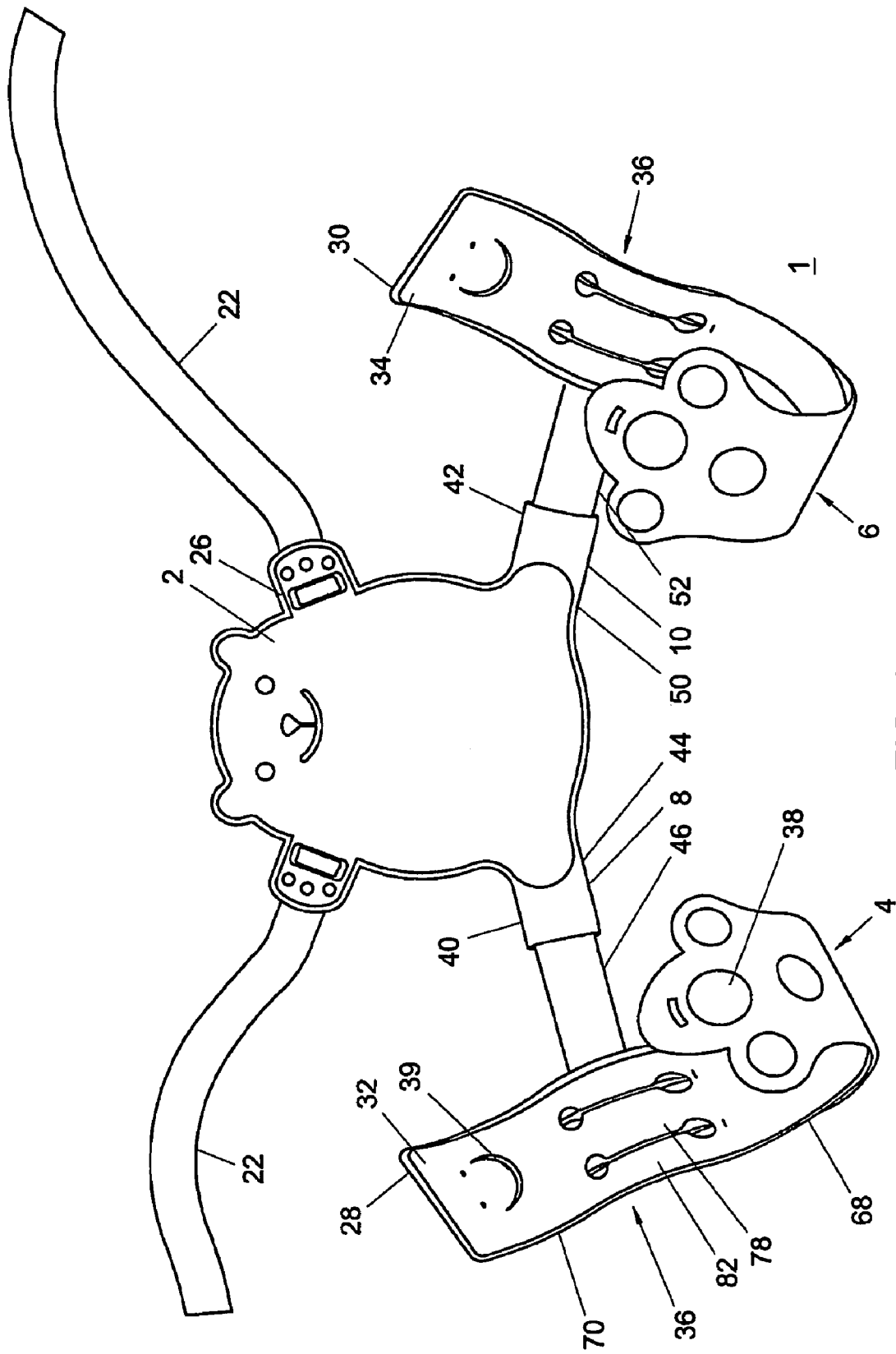
FIG. 1a shows a schematic front view of a hip abduction orthosis according to the invention.
Figure 1B:
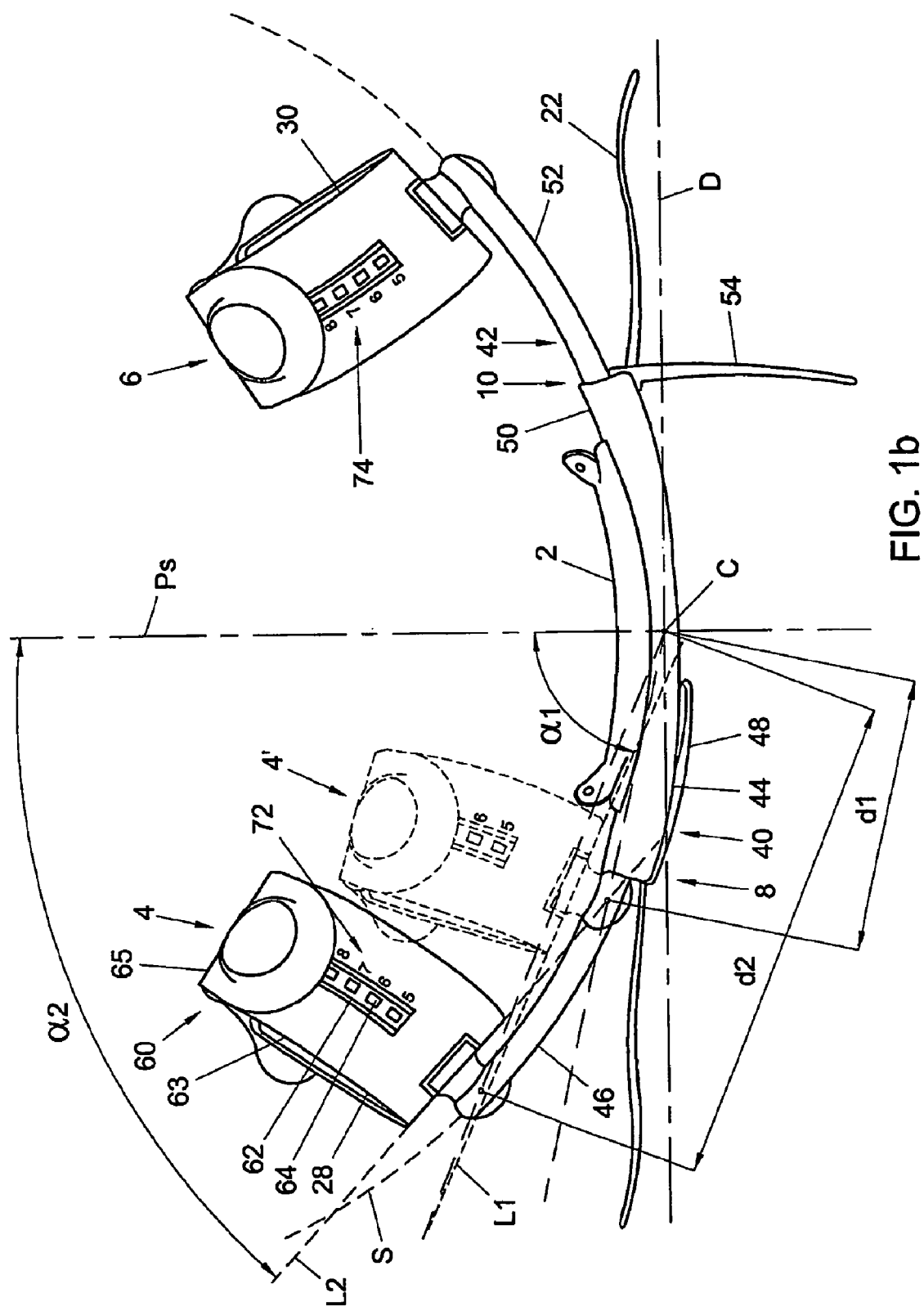
Figure 1C:
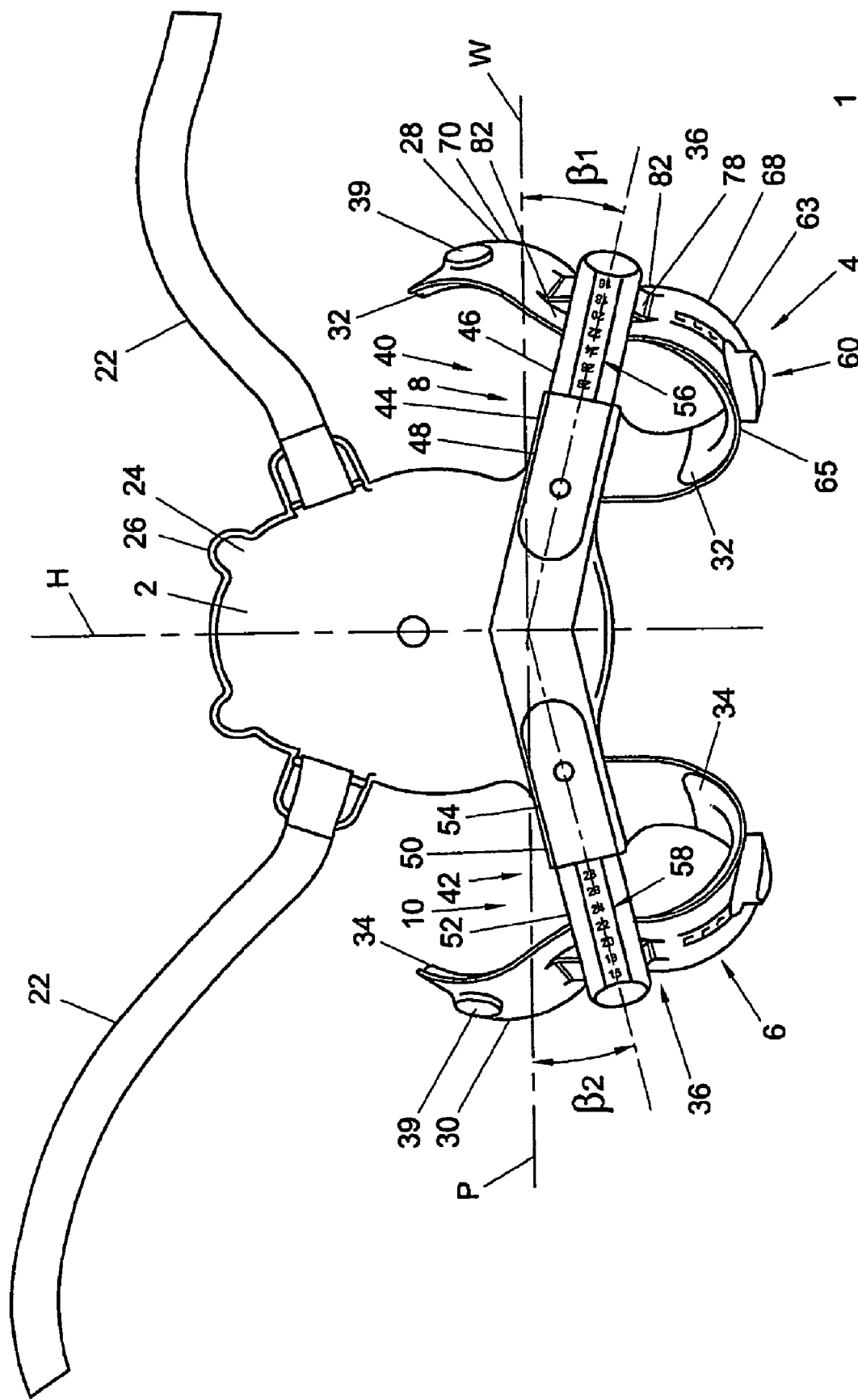
FIG. 1c shows a back view of the hip abduction orthosis shown in FIGS. 1a and 1b.

FIGS. 1a, 1b and 1c show an example of a first embodiment of a hip abduction orthosis 1 according to the invention. FIG. 1a shows a front view, FIG. 1b a bottom view and FIG. 1c a back view of the hip abduction orthosis 1. In FIGS. 1a-1c, the hip abduction orthosis 1 is provided with a trunk engaging part 2, a first and a second thigh engaging part 4, 6 and a first and a second coupling part 8, 10. The first coupling part 8 connects the first thigh engaging part 4 with the trunk engaging part 2. The second coupling part 10 connects the second thigh engaging part 6 with the trunk engaging part 2.

In this example, the first thigh engaging part 4 is rotationally connected with the first coupling part 8 about a (virtual) rotational axis extending transverse to the coupling part 8 in this example, in FIG. 1b substantially in the plane of the drawing and through the first thigh engaging part 4. In this example, the second thigh engaging part 6 is rotationally connected with the second coupling part 10 about a (virtual) rotational axis extending transverse to the coupling part 10 in this example, in FIG. 1b substantially in the plane of the drawing and through the second thigh engaging part 6. The rotational freedom of the thigh engaging parts has the advantage that the upper legs have some freedom of movement, which ensures a better blood flow of the hip balls, and consequently a more rapid recovery process. In addition, the rotational freedom offers the possibility that the user, for instance a baby, can crawl and the like, so that the normal development process of the user is not, at least hardly, limited.

In a special variant, the hip abduction orthosis 1 is provided with means for blocking the rotational freedom of the thigh engaging parts (not shown). This offers the possibility to use the hip abduction orthosis in the treatment of very specific disorders such as very specific luxations.

FIG. 1b shows a bottom view of the hip abduction orthosis 1 shown in FIGS. 1a and 1c. FIG. 1b shows that the coupling parts 8, 10 are designed as a first and second guide 40, 42. The first guide 40 comprises a sleeve 44 and an arm 46. In this example, the arm 46 is slidably received in the sleeve 44 for setting a distance between the first thigh engaging part 4 and the trunk engaging part 2. FIG. 1b shows the first thigh engaging part both in a first and in a second position with respect to the trunk engaging part 2. In the first position, the first thigh engaging part 4' is at a first distance $d_1$ from the trunk part 2. In the second position, the first thigh engaging part 4 is at a second distance $d_2$ from the trunk part 2. The distance between the first thigh engaging part and the trunk part is settable, in this example within a predetermined distance range. The distance range preferably has a length of more than 2 cm, more preferably more than 10 cm. The distance range preferably has a length of less than 30 cm, more preferably less than 20 cm.

In the first position in FIG. 1b, the first thigh engaging part is designated by reference numeral 4' and shown in broken lines. In the second position in FIG. 1b, the first thigh engaging part is designated by reference numeral 4 and shown in continuous lines. In use, generally the thigh engaging part 4' will be used in the first position with a smaller user than when the thigh engaging part 4 is placed in the second position. Thus, generally, as shown in FIG. 1b, the first thigh engaging part will be set to engage a thinner thigh when the distance between that thigh engaging part and the trunk engaging part is smaller (while of course variations are possible depending on, for instance, a build of the user).

The first coupling part 8 is further provided with locking means 48 for fixing the set distance. In this example, the locking means are designed as a quick release, but other locking means such as for instance a mortise and tenon joint or a toothing are also possible. The coupling part 8 of the hip abduction orthosis 1 may be arranged for steplessly setting the distance within a predetermined range of distances. The coupling part 8 of the hip abduction orthosis 1 may also be arranged for setting the distance in a plurality of steps. Here, a step of a plurality of steps is preferably smaller than 2.6 cm, more preferably smaller than 1.5 cm. A step of the plurality of steps is preferably larger than 0.2 cm, more preferably larger than 0.7 cm. Most preferably, a step of the plurality of steps is substantially equal to 1 cm. In this example, the second guide 42 of the second coupling part 10 is provided with a sleeve 50, an arm 52 and locking means 54 in a similar manner.

That the distance between the thigh engaging part and the trunk part is settable also has the advantage that the hip abduction orthosis can "grow" with the user, so that the same orthosis can be used during the whole treatment, and it is not necessary to buy another orthosis as soon as the user has grown slightly.

Herein, an abduction angle of the first thigh engaging part 4 is defined as the acute angle included between, on the one side, a line $L_1$ which operatively extends in the longitudinal direction of the first thigh 14 associated with the first thigh engaging part 4 and through a plane of the first thigh engaging part 4 which operatively abuts the first thigh 14 and, on the other side, the sagittal plane Ps of the hip abduction orthosis 1 which operatively coincides with the sagittal plane of the user 12. Likewise, herein, an abduction angle of the second thigh engaging part 6 is defined as the acute angle included between, on the one side, a line which operatively extends in the longitudinal direction of the second thigh 16 associated with the second thigh engaging part 6 and through a plane of the second thigh engaging part 6 which operatively abuts the second thigh 16 and, on the other side, the sagittal plane Ps.

FIG. 1b shows that the guides 40, 42 are arranged such that the thigh engaging parts 4, 6 are movable along a fixed predetermined path with respect to the trunk engaging part 2, in this example along a curved path, more specifically along an arc S. Thus, a change of the distance between the thigh engaging part and the trunk engaging part within a predetermined distance range results in a predetermined change of the abduction angle of the thigh engaging part. In this example, each change of the distance within the predetermined distance range results in a predetermined change of the abduction angle.

A radius of the arc S is preferably smaller than 500 mm, more preferably smaller than 350 mm. The radius of the arc is preferably larger than 100 mm, more preferably larger than 200 mm. Most preferably, the radius is substantially 250 mm. Thus, to each distance, an abduction angle is added which is particularly suitable for treating hip dysplasia and/or (sub) luxation in children. In addition, FIG. 1b shows that, in this example, the first and the second thigh engaging part 4, 6 are, at least in top plan view or bottom view, movable along substantially one and the same arc.

Since, in this example, the guides 40, 42 are arranged such that the thigh engaging parts 4, 6 are movable along the arc S with respect to the trunk engaging part 2, in the bottom view shown in FIG. 1b, an abduction angle α of the thigh engaging part 4 is fixed for a given distance d from the thigh engaging part 4 to a fixed point, for instance the center C, of the trunk engaging part 2. Likewise, in the bottom view shown in FIG. 1b, an abduction angle α of the thigh engaging part 6 is fixed for a given distance d from the thigh engaging part 6 to a fixed point, for instance the center C, of the trunk engaging part 2.

The hip abduction orthosis 1 in FIGS. 1a, 1b and 1c is thus arranged such that the distance d and the abduction angle α are coupled such that each set distance is coupled with a set abduction angle coupled therewith. More specifically, in this example, it holds that each set distance is unambiguously coupled with the set abduction angle coupled therewith. In the example, if the set distance increases, the set abduction angle coupled therewith decreases. In this example, the distance d and the abduction angle α are coupled such that the first and second thigh engaging part 4, 6 are movable along the arc S.

Since the distance d and the abduction angle α are coupled, it is not necessary to separately set the distance d and the abduction angle α.

More generally, it holds according to the invention that the distance d and the abduction angle α are coupled such that a first set distance $d_1$ between the at least one thigh engaging part 4, 6 and the trunk engaging part 2 is coupled with a first set abduction angle $\alpha_1$ and that a second set distance $d_2$ different from the first set distance $d_1$ is coupled with a second set abduction angle $\alpha_2$ different from the first set abduction angle $\alpha_1$. Thus, if the user sets the distance d at the first set distance $d_1$, the hip abduction orthosis itself sets the abduction angle α at the first set abduction angle $\alpha_1$. Further, if the user sets the distance d at the second set distance $d_2$, the hip abduction orthosis itself set the abduction angle α at the second set abduction angle $\alpha_2$. Thus, setting the distance d at the first set distance $d_1$ results in setting the abduction angle α at the first set abduction angle $\alpha_1$. Further, setting the distance d at the second set distance $d_2$ results in setting the abduction angle α at the second set abduction angle $\alpha_2$.

It is possible that at least one of the coupling parts 8 and/or 10 of the hip abduction orthosis 1, for instance the arm 46 and/or 52, is provided with a readjusting element (not shown) for slightly readjusting a position of the thigh engaging part 4 and/or 6 close to the position of the thigh engaging part 4, 6 determined by the set distance and the set abduction angle coupled therewith. The arm 46 and/or 52 may, for instance, be provided with a bending element for setting a bending angle between at least a part of the respective coupling part 8 and/or 10, respectively, and the trunk engaging part 2. In that case, with the aid of such a bending element, it is possible to slightly adjust the position of the thigh engaging part 4 and/or 6, respectively, to the situation, for instance to the body of the user and/or a medical indication. Thus, a fine setting of the position of the thigh engaging part 4 and/or 6 can be provided. Preferably, the bending element is arranged to be bent, such that the bending element remains in the bent condition after bending. Alternatively, the bending element is arranged for adjusting the position of the thigh engaging part 4 and/or 6 in a plurality of discrete steps.

FIG. 1c shows that the guides 40, 42 recede in lateral direction downwards away from a transversal plane P which operatively extends substantially through the hip balls of the user 12. An angle $\beta_1$ included between the transversal plane P and the guide 40 is preferably smaller than 20°, more preferably smaller than 15°. The angle $\beta_1$ is preferably larger than 2°, more preferably larger than 7°. Most preferably, the included angle $\beta_1$ is substantially 12°. In a similar manner, the above holds for an angle $\beta_2$ included between the transversal plane P and the guide 42. Thus, in this example, for both hip joints, a predetermined flexion angle is prescribed. The flexion and abduction for both hip joints together determine a straddle of the thighs 14, 16 in use.

In an exemplary embodiment, for both thigh engaging parts 4, 6, the abduction angle is fixed in that the first and the second thigh engaging part 4, 6 are, at least in top plan view or bottom view, movable long substantially one and the same arc, with preferably a radius of substantially 250 mm and, for both thigh engaging parts 4, 6, the flexion angle is fixed in that the angle included between the transversal plane P and guide 40 is substantially 12°. With the above-mentioned exemplary embodiment, for both thighs 14, 16, a particularly favorable straddle is obtained for treating hip dysplasia.

It will be clear that, in this example, when the distance between the first and/or second thigh engaging part 4, 6 and the trunk engaging part 2 increases, a height position of the first and/or second thigh engaging part, respectively, decreases in a direction from the hip to the head of the user. In this example, it therefore holds that the distance d, the abduction angle α and the height position are coupled. The distance d, the abduction angle α and the height position are coupled such that the first and/or second thigh engaging part 4, 6 is movable along a fixed predetermined path with respect to the trunk engaging part 2. In this example, the fixed predetermined path recedes in lateral direction downwards away from the transversal plane P.

More generally, it holds that the distance d, the abduction angle α and the height position of the first and/or the second thigh engaging part 4, 6 are coupled such that the first set distance $d_1$ between that thigh engaging part and the trunk engaging part is coupled with the first set abduction angle $\alpha_1$ and a first set height position and the second set distance $d_2$ different from the first set distance $d_1$ is coupled with the second set abduction angle $\alpha_2$ different from the first set abduction angle $\alpha_1$ and a second set height position optionally different from the first set height position.

It will be clear that it is possible for the angle $\beta_1$ and/or $\beta_2$ to be designed to be settable. Thus, the flexion angle of one or both hip joints is designed to be settable. It is also possible that the height position of the thigh engaging part 4, 6 is designed to be settable in a different manner. Due to the settable height position, the hip abduction orthosis cannot only be used for normal hip dysplasia but also for more specific hip disorders.

Figure 2:
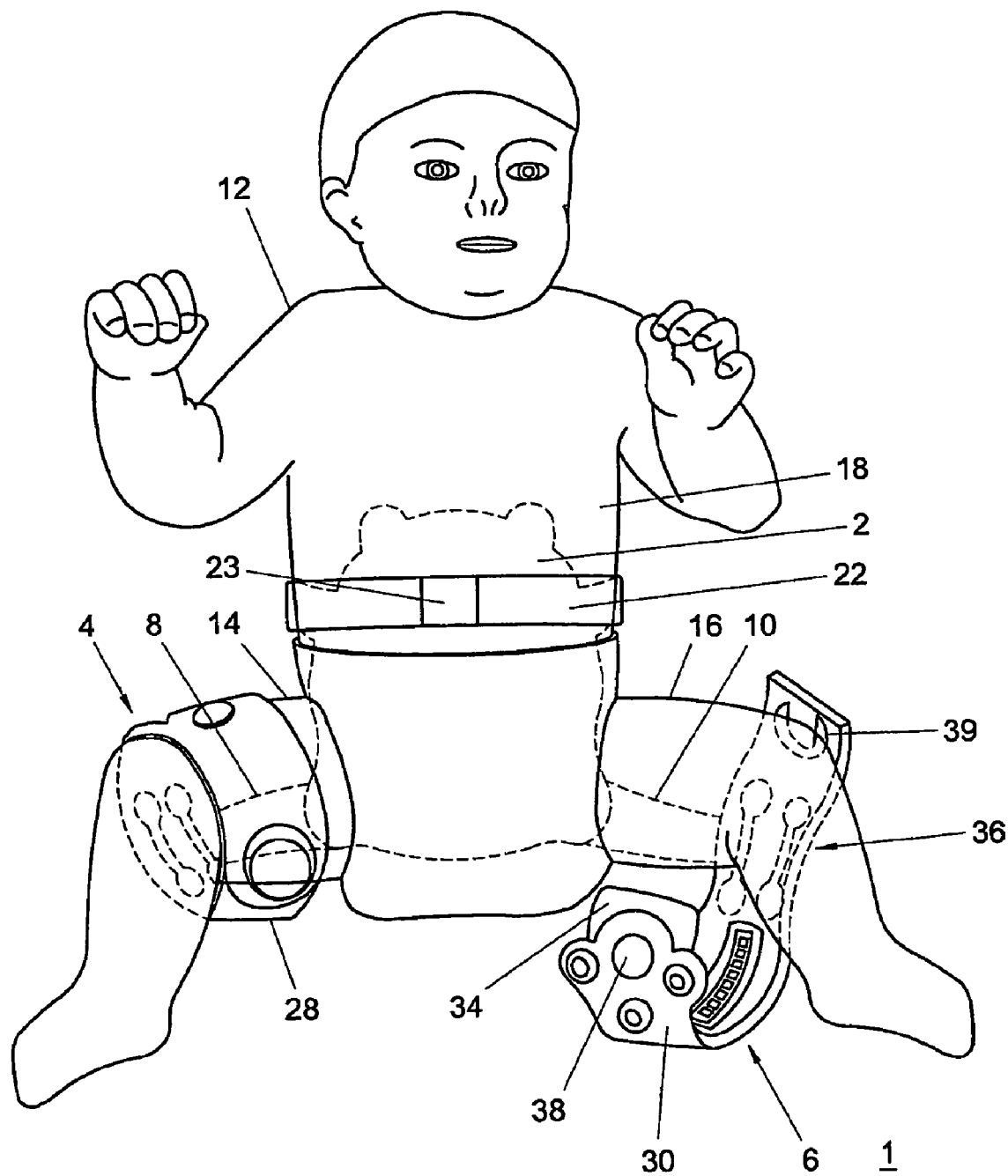
FIG. 2 shows a front view of the hip abduction orthosis shown in FIGS. 1a-1c applied to a user.

FIG. 2 shows a front view of the example of the hip abduction orthosis shown in FIGS. 1a-1c applied to a user 12, in this example a small child. Here, parts of the hip abduction orthosis 1, which are behind the user in the front view of FIG. 2, are shown in broken lines. The first thigh engaging part 4 engages a first thigh 14 of the user 12. The second thigh engaging part 6 engages a second thigh 16 of the user 12. In the example of FIG. 2, the first thigh engaging part 4 is connected with the first thigh 14. In the example of FIG. 2, the second thigh engaging part 6 is not connected with the second thigh 16. In normal use, the second thigh engaging part 6 will be connected with the second thigh 16, as shown with regard to the first thigh engaging part 4 in FIG. 2. The trunk engaging part 2 engages a trunk 18 of the user.

The hip abduction orthosis 1 is, for instance, used for treating hip dysplasia or for stabilizing a hip after luxation or subluxation, for instance with small children, such as babies or toddlers. The first and the second coupling part 8 and 10 are arranged for substantially fixing a position of at least one first fixing point of the first thigh engaging part 4 and a position of at least one second fixing point of the second thigh engaging part 6, respectively, in a first and second position, respectively, with respect to the trunk engaging part. When the orthosis 1 is worn by a user 12, this means that a position of the thighs 14, 16 with respect to the trunk 18 is fixed. As a result, the hip joints are stabilized.

In the example of FIG. 2, the trunk engaging part 2 is positioned on the back side 20 of the trunk 18 of the user 12. In this example, the orthosis 1 is arranged such that the trunk engaging part 2 can be attached to the back side 20 of the trunk 18 of the user 12. Here, the trunk engaging part 2 extends substantially in a height direction H extending substantially parallel to a spine of the user 12, and the trunk engaging part 2 also extends substantially in a width direction W, which width direction W operatively substantially extends in a lateral direction with respect to the user 12 transversely to the height direction H. Since, in this example, the trunk engaging part 2 leaves a front side of the trunk 18 substantially free, the user 12 is not, at least less, hindered in carrying out tasks which take place on the front side of the trunk 18, such as for instance playing in case of children. The hip abduction orthosis 1 is provided with a band 22 for attaching the trunk engaging part 2 to the trunk 18. To this end, the band 22 may, for instance, be provided with a closure 23 known per se like Velcro, a buckle or a snap connection.

In this example, the trunk engaging part 2 is provided with a substantially rigid back support 24. Here, the substantially rigid back support 24 is sufficiently rigid to be able to sufficiently strongly connect the orthosis 1 with the trunk 18 in order to be able to fix the position of the thigh 14, 16 with respect to the trunk 18. In this example, the back support is also sufficiently supple to follow a shape of the back, for instance a curve of the spine, of the user. In this example, the first and the second coupling part 8, 10 are directly connected with the substantially rigid back support 24 in order to be able to connect the orthosis 1 sufficiently strongly with the trunk in order to be able to fix the position of the thigh 14, 16 with respect to the trunk 18. In order to increase the wearing comfort, in this example, the trunk engaging part 2 is further provided with a back cushion 26 which has an, at least slightly, flexible and/or elastic design and is provided on the side of the trunk engaging part 2 which operatively faces the trunk 18. Here, the back cushion 26 may extend outside a perimeter of the back support 24, and/or edges of the back support may have such a design, for instance rounded, that the edges of the back support 24 do not, at least less, uncomfortably press against the back side of the trunk 18 of the user 12.

In FIGS. 1a, 1b, 1c and 2, the thigh engaging parts 4 and 6 are each provided with a substantially rigid cuff 28 or 30, respectively. In use, the cuffs 28 and 30 enclose the first and the second thigh 14, 16, respectively. FIG. 1b shows that the cuffs 28, 30 of the thigh engaging parts 4, 6 have a conical shape, so that they follow a shape of the thighs 14, 16 of the user 12. This makes it possible to be able to sufficiently strongly connect the thigh engaging parts 4, 6 with the thighs 14, 16 in order to be able to fix the position of the thighs 14, 16 with respect to the trunk 18. In this example, the thigh engaging parts 4, 6 are each provided with a thigh cushion 32, 34 which has an, at least slightly, flexible and/or elastic design and is provided on the side of the thigh engaging part 4, 6 which operatively faces the thigh 14, 16. That is to say that the thigh cushion 32 is operatively included between the cuff 28 and the thigh 14 and that the thigh cushion 34 is operatively included between the cuff 30 and the thigh 16.

Thus, the back support 24 of the trunk engaging part 2 and the cuffs 28, 30 of the thigh engaging parts 4, 6 form substantially rigid molded parts which may, for instance, be manufactured from a substantially rigid plastic. The back cushion 26 and the thigh cushions 32, 34 may be manufactured from a flexible and/or elastic plastic. It will be clear that the properties of the plastic from which the molded parts can be manufactured differ from the properties of the plastic from which the cushions can be manufactured.

It is possible that the trunk engaging part, comprising the plastic back support 24 and the plastic back cushion 26, and/or the thigh engaging part 4 and/or 6, comprising the plastic cuff 28 and/or 30 and the plastic thigh cushion 32 and/or 34, respectively, are manufactured by means of multi-component injection molding, for instance two-component injection molding (also known as 2K injection molding). Thus, the cushion and the molded part are formed simultaneously, which allows an inexpensive manufacture of the thigh engaging part and/or trunk engaging part.

In addition to the above-mentioned thigh engaging parts and trunk engaging part, the coupling parts, for instance the arm and sleeve, as shown in FIG. 1c, may also be manufactured from plastic.

In a special embodiment, the hip abduction orthosis is substantially completely manufactured from plastic. Preferably, the hip abduction orthosis is completely manufactured from plastic. Thus, an orthosis is provided which can be manufactured simply and inexpensively. In addition, this orthosis can be cleaned simply and thoroughly, for instance with water and optionally a cleansing agent, such as for instance standard dishwashing liquid, or even in a standard dishwasher. The possibility to simply and thoroughly clean the hip abduction orthosis is particularly favorable if the orthosis is used by a small child. This is because it is possible, and even probable, that, in that case, the orthosis becomes dirty due to, for instance, foods, urine and/or excreta, which makes thorough cleaning of the orthosis necessary in order to not endanger the general health of the child.

It will be clear that using multi-component injection molding for obtaining combined molded parts and cushions may also be used for parts which are in contact with the body of a user with other hip abduction orthoses and other orthoses.

It will also be clear that it is also possible to manufacture other hip abduction orthoses and other orthoses completely from plastic, for instance if it is necessary to be able to simply and thoroughly clean those orthoses.

The hip abduction orthosis 1 described so far can be set as follows in order to correspond with dimensions of the user 12.

The first thigh engaging part 4 is placed at a desired distance from the trunk engaging part 2 and/or at a desired abduction angle. In the example of the hip abduction orthosis 1 shown in FIGS. 1a, 1b, 1c and 2, the locking means 48 of the first coupling part 8 are unlocked and the first thigh engaging part 4 is placed at the desired distance from the trunk engaging part 2. In this example, the arm 46 can then be moved in the sleeve.

As shown in FIG. 1c, the hip abduction orthosis 1 may be provided with first distance indicating means 56 for showing an indication of the set distance between the first thigh engaging part 4 and the trunk engaging part 2, for instance the set distance, for instance in centimeters. In FIG. 1c, the distance indicating means 56 are designed as a graduation provided on the arm 46 of the first coupling part 8.

Further, the second thigh engaging part 6 is placed at a desired distance from the trunk engaging part 2 and/or at a desired abduction angle for the second thigh 16. This takes place in similar manner to what was described hereinabove with regard to the first thigh engaging part 4. The hip abduction orthosis may further be provided with second distance indicating means 58 for showing an indication of the set distance between the second thigh engaging part 6 and the trunk engaging part 2, for instance the set distance, for instance in centimeters.

In a special embodiment, a distance can be determined, for instance measured with a tape measure, between a first back of the knee of the first thigh 14 and a second back of the knee of the second thigh 16 if the two thighs 14, 16 have the right abduction, and are or are kept preferably in the right straddle. Here, it for instance holds for each leg that the hip ball is placed centrally in the socket of the hip. Here, use can be made of X-rays or the experience of an expert, for instance a doctor. The first and second thigh engaging part 4, 6 can then be placed at such a distance from the trunk engaging part 2 that the first and the second thigh 14, 16 operatively have the desired abduction, for instance such that a distance between the first and the second back of the knee operatively corresponds with the determined distance between the first and the second back of the knee. The hip abduction orthosis may then be provided with distance indicating means, for instance the graduations 56, 58, which show the determined or measured distance between the backs of the knees corresponding with a set distance between a thigh engaging part and the trunk engaging part.

A first circumferential dimension of the first thigh engaging part 4 is adjusted to a circumferential dimension of the firs thigh 14. To this end, the first thigh engaging part 4 is provided with first circumference setting means 60. The circumference setting means 60 may be arranged for steplessly setting the circumferential dimension within a predetermined range of circumferential dimensions. The circumference setting means 60 may also be arranged for setting the circumferential dimension in a plurality of steps. Here, a step of the plurality of steps is preferably smaller than 2.6 cm, more preferably smaller than 1.5 cm. A step of the plurality of steps is preferably larger than 0.2 cm, more preferably larger than 0.7 cm. Most preferably, a step of the plurality of steps is substantially equal to 1 cm. In FIG. 1b, the circumference setting means 60 comprise a strip 62 provided with a plurality of spaced recesses 64 and an engaging element 66 for engaging one of the recesses 64. It will be clear that, in this example, the first thigh engaging part is provided with a first subpart 63 connected with the strip 62 and a second subpart 65 connected with the engaging element 66.

The circumferential dimension of the first thigh 14 is determined, for instance measured with a tape measure. Then, with the aid of the circumference setting means 60, the circumferential dimension of the first thigh engaging part is set such that it corresponds with the circumferential dimension of the first thigh 14.

In an alternative embodiment, the circumference setting means 60 are arranged such that they lock themselves in or near the set circumferential dimension. To this end, the circumference setting means may, for instance, be provided with a toothing. Such circumference setting means are known per se and are, for instance, used in ski boots.

As shown in FIG. 1b, the hip abduction orthosis 1 may be provided with first circumference indicating means 72 for showing an indication of the set circumferential dimension of the first thigh engaging part 4, for instance the set circumferential dimension, for instance in centimeters. In FIG. 1b, the circumference indicating means 72 are designed as a graduation provided on the first subpart 68 of the first thigh engaging part 4.

Further, a second circumferential dimension of the second thigh engaging part 6 is adjusted to a circumferential dimension of the second thigh 16. This takes place in a similar manner to what was described hereinabove with regard to the first thigh engaging part 4. The hip abduction orthosis may further be provided with second circumferential indicating means 74 for showing an indication of the set circumferential dimension of the second thigh engaging part 6, for instance the set circumferential dimension, for instance in centimeters.

In the examples of FIGS. 1a, 1b, 1c and 2, further, the thigh engaging parts 4, 6 are each provided with a bistable element 36. The bistable element 36 has two stable conditions. In a first stable condition, the bistable element 36 keeps the thigh engaging part 4, 6 opened, so that a thigh can be placed in the thigh engaging part without the thigh engaging part falling shut or otherwise hindering the access for the thigh. In a second stable condition, the bistable element 36 keeps the thigh engaging part 4, 6 substantially closed, so that the thigh 14, 16 is at least partly enclosed by the thigh engaging part 4, 6.

Figure 3A:
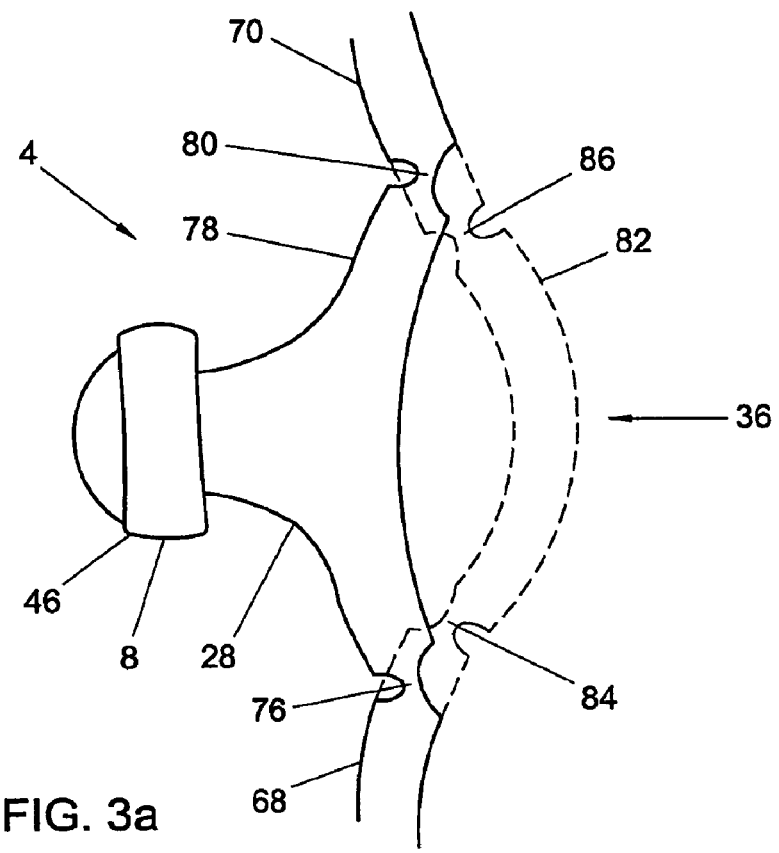
FIG. 3a shows a side elevational view of a detail of a thigh engaging part in a first stable condition.
Figure 3B:
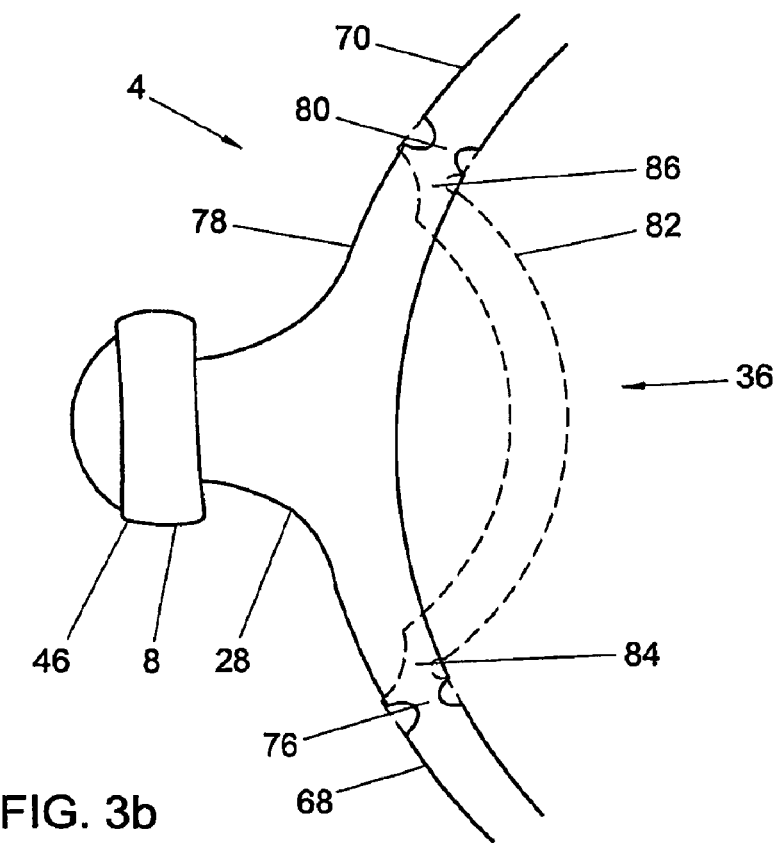
FIG. 3b shows a side elevational view of the detail of the thigh engaging part shown in FIG. 3a in a second stable condition.

FIGS. 3a and 3b show a side elevational view of a detail of the thigh engaging part 4 in the first and the second stable condition, respectively. In FIGS. 3a and 3b, a first enclosing part 68 of the thigh engaging part 4 is pivotally connected with an intermediate part 78 of the thigh engaging part 4 about a (virtual) rotational axis, which intermediate part 78 is connected with the first coupling part 8. In FIGS. 3a and 3b, a second enclosing part 70 of the thigh engaging part 4 is pivotally connected with the intermediate part 78 of the thigh engaging part 4 about a (virtual) rotational axis 80. In this example, the first and the second enclosing part 68, 70 are bendably pivotally connected with the intermediate part 78. Thus, the first and second enclosing part 68, 70 and the intermediate part 78 can be manufactured as one whole, for instance by means of injection molding.

In this example, the bistable element 36 of the first thigh engaging part 4 comprises at least one resilient element 82 (in FIG. 1a, it can be seen that, in this example, the bistable element 36 comprises two resilient elements 82). The resilient elements 82 are pivotally connected with the first enclosing part 68 about a (virtual) rotational axis 84 and pivotally connected with the second enclosing part 70 about a (virtual) rotational axis 86. In this example, the first and the second enclosing part 68, 70 are bendably pivotally connected with the resilient elements 82. Thus, the first and second enclosing part 68, 70 and the resilient element 82 can be manufactured as one whole, for instance by means of injection molding.

FIGS. 3a and 3b show that a distance between the (virtual) rotational axes 84 and 86 is smaller than a distance between the (virtual) rotational axes 76 and 80. Here, a length of the resilient elements 82 can be chosen such that, in the first and the second stable condition, the resilient elements 82 experience substantially no tensile stress and/or compressive stress. It will be clear that, if the first and/or the second enclosing part 68, 70 is in a rotational position between the first and the second stable condition, the resilient elements 82 will experience a compressive stress, and will possibly bend or buckle as a result. Since the resilient elements will attempt to counteract the compressive stress, that first and/or second enclosing part 68, 70 will be moved to the first and/or second stable condition.

The hip abduction orthosis 1 described so far can be applied to the user 12, in this example a small child, as follows.

First, the hip abduction orthosis 1 can be made ready to be applied to the user 12. To this end, the bistable elements 36 of the two thigh engaging parts 4, 6 are brought into the first stable condition. Further, the hip abduction orthosis 1 can be placed on a base, for instance on a table, by a back side of the trunk engaging part 2.

Then, the user 12 can be placed on the hip abduction orthosis 1 from above, such that the upper legs 14, 16 of the user 12 are at the height of the thigh engaging parts 4, 6. By (carefully) pressing the upper legs 14, 16 of the user 12 into the thigh engaging parts 4, 6, the bistable elements 36 will go from the first stable condition to the second stable condition, and the thigh engaging parts 4, 6 will, at least partly, enclose the upper legs 14, 16 of the user 12. In the example of FIG. 3a, it can be seen that, in the side elevational view shown, the resilient elements 82 project outside an outline of the intermediate part 78. It will be clear that, if the upper leg 14 presses against the resilient elements 82, the bistable element 36 will go from the first stable condition to the second stable condition.

Thus, the hip abduction orthosis is positioned with respect to the user 12. Due to the thigh engaging parts 4, 6 at least partly enclosing the upper legs 14, 16 in the second stable condition, the risk of a thigh engaging part and the upper leg associated therewith separating from each other again (for instance by thrashing about of the child) is reduced.

Then, the thigh engaging parts can be closed by means of a closure 38, 39. In the example, to this end, the thigh engaging parts 4, 6 are provided with a snap closure.

If the thigh engaging parts are provided with the circumference setting means which are arranged such that they lock themselves in or near the set circumferential dimension, it is also possible for the thigh engaging parts to be set at the largest possible circumferential dimension. Then, the closure 38, 39 can be closed. Finally, the circumferential dimension of the thigh engaging parts can be set by reducing the circumferential dimension until the thigh engaging parts enclose the upper leg as desired. The thigh engaging parts will lock themselves in or near the set circumferential dimension.

Finally, the band 22 of the trunk engaging part 2 can be provided around the trunk 18 and be closed by means of a closure.

In FIGS. 1a-1b and 2, first thigh engaging part 4 is connected with the second thigh engaging part 6 exclusively via the first and second coupling part 8, 10. In use, forces on the orthosis are therefore transmitted from the first thigh engaging part 4 to the thigh engaging part 6 exclusively via the first and second coupling part 8, 10. In this example, the first thigh engaging part 4 is then connected with the second thigh engaging part 6 exclusively via a back side of the orthosis 1. The back side of the orthosis 1 operatively extends on the back side 20 of the trunk 18 of the user 12. In use, forces are thus transmitted from the first thigh engaging part 4 to the second thigh engaging part 6 exclusively via a back side of the orthosis. The orthosis 1 is thus free from the coupling parts 8, 10 on the front side of the trunk 18. Also due to this, the user 12 is less hindered in carrying out tasks which take place on the front side of the trunk 18.

In the example of FIGS. 1a, 1b, 1c and 2, both the trunk engaging part 2 and the coupling parts 8, 10 are, in use, on the back side 20 of the trunk 18, which is favorable to the wearing comfort of the orthosis 1. Further, this makes the applying and removing the orthosis 1 with the user 12 simpler, since the orthosis can simply be applied or removed from the back side 20 of the trunk 18.

In the examples, the hip abduction orthosis is provided with a design which is suitable for children. In this case, the hip abduction orthosis is designed as a teddy bear. This offers the advantage that the acceptation of the hip abduction orthosis by the user, for instance if this is a (small) child, and/or by a caretaker of the user, for instance a parent, will be greater. Thus, it is simpler for a caretaker of the user to attach the hip abduction orthosis to the user. It will be clear that the hip abduction orthosis may also be provided with a different appearance, for instance a clown, a different (cuddly) animal, a prince/princess, a fairy-tale figure, a fantasy figure and the like.

In the examples, the trunk engaging part is connectable with the trunk of the user by means of a band. It is also possible for the trunk engaging part to comprise at least one bistable element for keeping the trunk engaging part open in a first stable condition for being able to place the trunk therein and keeping the trunk engaging part at least partly closed in a second stable condition for at least partly enclosing the trunk. In the example of FIG. 1a, for instance, the forepaws of the bear may have such a length, and may each be provided with a bistable element, that, in a first stable condition, the forepaws are wide open for being able to place the trunk engaging part to the trunk of the user and, in a second stable condition, "embrace" the user so that the trunk engaging part is attached to the trunk.

Such variations are all understood to fall within the framework of the invention.

The invention claimed is:

1. A hip abduction orthosis for stabilizing the hip joints of a user, comprising:
   a trunk engaging part arranged to be connected with a trunk of a user;
   a first thigh engaging part arranged for engaging a thigh of a user; and
   a first coupling part connects the first thigh engaging part connecting to the trunk engaging part;
   wherein a distance defined between the first thigh engaging part and the trunk engaging part is settable, an abduction angle of the first thigh engaging part is defined between a line operatively extending in the longitudinal direction of a thigh associated with the first thigh engaging part and through a plane of the first thigh engaging part operatively abutting the thigh and a sagittal plane;
   wherein the hip abduction orthosis is provided with distance indicating means for indicating the set distance between the first thigh engaging part and the trunk engaging part or a set abduction angle.

2. The hip abduction orthosis according to claim 1, wherein a change of the distance within a predetermined distance range results in a predetermined change of the abduction angle.

3. The hip abduction orthosis according to claim 2, wherein each change of the distance within the predetermined distance range results in a predetermined change of the abduction angle.

4. The hip abduction orthosis according to claim 3, wherein the distance and the abduction angle are set such that, if the set distance increases, the abduction angle coupled therewith decreases.

5. The hip abduction orthosis according to claim 2, wherein the distance range has a length of more than 10 cm.

6. The hip abduction orthosis according to claim 2, wherein the distance range has a length of less than 20 cm.

7. The hip abduction orthosis according to claim 2, wherein the distance range comprises a predetermined curved path.

8. The hip abduction orthosis according to claim 1, wherein a height position of the first thigh engaging part is settable in a height direction of a user.

9. The hip abduction orthosis according to claim 8, wherein the distance, the abduction angle and the height position are coupled such that the first set distance between the first thigh engaging part and the trunk engaging part is coupled with the first set abduction angle and a first set height position and the second set distance different from the first set distance is coupled with the second set abduction angle different from the first set abduction angle and a second set height position different from the first set height position.

10. The hip abduction orthosis according to claim 9, wherein the distance, the abduction angle and the height position are coupled such that the first thigh engaging part is movable along a fixed predetermined path with respect to the trunk engaging part.

11. The hip abduction orthosis according to claim 10, wherein the fixed predetermined path recedes in lateral direction downwards away from a transversal plane through the hip balls of a user.

12. The hip abduction orthosis according to claim 11, wherein an angle defined between the transversal plane and the predetermined path is smaller than 20 degrees.

13. The hip abduction orthosis according to claim 12, wherein an angle included between the transversal plane and the predetermined path is larger than 2 degrees.

14. The hip abduction orthosis according to claim 1, wherein the distance and the abduction angle are coupled such that each set distance is coupled with an abduction angle coupled therewith.

15. The hip abduction orthosis according to claim 14, wherein the distance and the abduction angle are coupled such that, with respect to the trunk engaging part, the first thigh engaging part is movable along a curved path.

16. The hip abduction orthosis according to claim 15, wherein, at least in top plan view, the first thigh engaging part is movable along one and the same arc.

17. The hip abduction orthosis according to claim 15, wherein a radius of the arc is smaller than 500 mm.

18. The hip abduction orthosis according to claim 1, wherein the hip abduction orthosis is arranged for setting the distance between the first thigh engaging part and the trunk engaging part in a plurality of steps.

19. The hip abduction orthosis according to claim 18, wherein a radius of the arc is larger than 100 mm.

20. The hip abduction orthosis according to claim 18, wherein a step of the plurality of steps is smaller than 2.6 cm.

21. The hip abduction orthosis according to claim 18, wherein a step of the plurality of steps larger than 0.2 cm.

22. The hip abduction orthosis according to claim 1, wherein the first thigh engaging part is rotatable about a rotational axis with respect to the first coupling part.

23. The hip abduction orthosis according to claim 22, wherein the first thigh engaging part is connected with that at least one coupling part via a pivot which directly engages the first thigh engaging part.

24. The hip abduction orthosis according to claim 22, wherein the rotational axis extends through that the first thigh engaging part.

25. The hip abduction orthosis according to claim 1, wherein a circumferential dimension of the first thigh engaging part is settable.

26. The hip abduction orthosis according to claim 25, wherein the first thigh engaging part is provided with circumference setting means arranged to lock in or near the set circumferential dimension.

27. The hip abduction orthosis according to claim 25, wherein the first thigh engaging part is provided with circumference indicating means for showing an indication of the set circumferential dimension.

28. The hip abduction orthosis according to claim 1, wherein the abduction angle of the first thigh engaging part is settable, and the distance and the abduction angle are coupled such that a first set distance between the first thigh engaging part and the trunk engaging part are coupled with a first set abduction angle and a second set distance different from the first set distance is coupled with a second set abduction angle different from the first set abduction angle.

29. The hip abduction orthosis according to claim 28, wherein the first coupling part is provided with a guide for guiding the first thigh engaging part from the first set distance and the first set abduction angle coupled therewith to the second set distance and the second set abduction angle coupled therewith.

30. The hip abduction orthosis according to claim 1, wherein the first thigh engaging part comprises a bistable element for keeping the first thigh engaging part open in a first stable condition for placing a thigh therein and keeping the first thigh engaging part substantially closed in a second stable condition for at least partly enclosing a thigh.

31. The hip abduction orthosis according to claim 30, wherein the bistable element comprises a resilient element.

32. The hip abduction orthosis according to claim 1, wherein the orthosis is arranged for operatively transmitting the force from the first thigh engaging part to a second thigh engaging part arranged for engaging a second thigh of a user exclusively via a back side of the orthosis extending on a back side of a user.

33. The hip abduction orthosis according to claim 32, wherein the first thigh engaging part is connected to the second thigh engaging part exclusively via a back side of the orthosis.

34. The hip abduction orthosis according to claim 1, wherein the hip abduction orthosis is arranged for steplessly setting the distance between the first thigh engaging part and the trunk engaging part.

35. The hip abduction orthosis according to claim 1, wherein the first coupling part is arranged for substantially fixing at least one first fixing point of the first thigh engaging part and at least one second fixing point of a second thigh engaging part arranged for engaging a second thigh of a user, in a first or second position, respectively, with respect to the trunk engaging part.

36. The hip abduction orthosis according to claim 1, wherein each set distance is unambiguously coupled with the set abduction angle coupled therewith.

37. The hip abduction orthosis according to claim 1, wherein the hip abduction orthosis is provided with locking means for fixing the set distance.

38. The hip abduction orthosis according to claim 1, wherein the distance indicating means indicate a distance between two backs of the knees of a user corresponding with the set distance.

39. The hip abduction orthosis according to claim 1, wherein the first thigh engaging part has a conical shape when it has been applied to a thigh of a user.

40. The hip abduction orthosis according to claim 1, wherein the first thigh engaging part and the trunk engaging part comprises a substantially rigid molded part manufactured from plastic.

41. The hip abduction orthosis according to claim 1, wherein the first thigh engaging part and the trunk engaging part is provided with a cushion from a flexible or elastic material operatively facing a user.

42. The hip abduction orthosis according to claim 1, wherein, in use, the trunk engaging part is on a back side of a user, wherein the trunk engaging part extends in a height direction operatively extending substantially parallel to a spine of a user, and wherein the trunk engaging part extends in a width direction operatively extending in a lateral direction with respect to a user.

43. The hip abduction orthosis according to claim 1, wherein the trunk engaging part is provided with a band for operatively attaching the trunk engaging part to the trunk of a user.

44. The hip abduction orthosis according to claim 1, wherein the trunk engaging part comprises at least one bistable element for keeping the trunk engaging part open in a first stable condition for being able to place the trunk therein and keeping the trunk engaging part substantially closed in a second stable condition for at least partly enclosing the trunk.

45. An orthosis for stabilizing a joint of a user, comprising:
a base engaging part arranged to be connected with a body portion of a user;
a first body engaging part arranged for engaging a body part of a user, the first body engaging part defining first and second end portions and an intermediate portion therebetween; and
a first coupling part connects the first body engaging part to the base engaging part;
wherein a distance defined between the first body engaging part and the base engaging part is settable, a first angle of the first body engaging part is defined between a line operatively extending in the longitudinal direction of the body part associated with the first body engaging part and through a plane of the first body engaging part operatively abutting that body part and a sagittal plane.

46. The orthosis according to claim 45, further comprising:
a bistable element belonging to the limb engaging part and arranged to maintain the limb engaging part open in a first stable condition for placing a limb therein and maintain the limb engaging part substantially closed in a second stable condition for at least partly enclosing the body part.

47. The orthosis according to claim 46, wherein the intermediate portion of the first body engaging part connects to the first coupling part, the first and second end portions extending freely from the first coupling part, the first and second portions arranged to move relative to the first coupling part when moving from the first and second stable conditions.

48. The orthosis according to claim 47, wherein the first body engaging part includes a first enclosing part bendably pivotally connected to an intermediate part about a first virtual axis.

49. The orthosis according to claim 48, wherein the bistable element is bendably pivotally connected to the first enclosing part about a second virtual rotational axis.

50. The orthosis according to claim 46, wherein the first and second end portions of the engaging part have closure devices arranged to secure the first and second end portions to one another.

51. An orthosis comprising:
an engaging part arranged to at least partly operatively enclose a body part of a user, the engaging part defining first and second end portions and an intermediate portion therebetween;
a bistable element belonging to the engaging part and arranged to maintain the engaging part open in a first stable condition for placing the body part therein and maintain the engaging part substantially closed in a second stable condition for at least partly enclosing the body part;
wherein the engaging part includes a first enclosing part bendably pivotally connected to an intermediate part about a first virtual axis.

52. The orthosis according to claim 51, wherein the engaging part depends from a frame structure and is arranged to secure the frame structure to a body portion of the wearer.

53. The orthosis according to claim 52, wherein the intermediate portion of the engaging part connects to the frame structure, the first and second end portions extending freely from the frame structure, the first and second portions arranged to move relative to the frame structure when moving from the first and second stable conditions.

54. The orthosis according to claim 51, wherein the bistable element is bendably pivotally connected to the first enclosing part about a second virtual rotational axis.

55. The orthosis according to claim 51, wherein the first and second end portions of the engaging part have closure devices arranged to secure the first and second end portions to one another.

* * * * *